//  US005913852A

United States Patent [19]
Magram

[11] Patent Number: 5,913,852
[45] Date of Patent: Jun. 22, 1999

[54] DRAIN CANNULA

[75] Inventor: Gary Magram, Baltimore, Md.

[73] Assignee: Nemours Foundation, Jacksonville, Fla.

[21] Appl. No.: 08/959,508

[22] Filed: Oct. 28, 1997

Related U.S. Application Data

[63] Continuation-in-part of application No. 08/505,807, Jul. 21, 1995, Pat. No. 5,772,261.

[51] Int. Cl.$^6$ ..................................................... A61M 1/00
[52] U.S. Cl. .......................... 604/540; 604/524; 604/533; 604/284
[58] Field of Search ................................. 604/8–10, 280, 604/282–284, 49, 540, 524, 533; 138/DIG. 8

[56] References Cited

U.S. PATENT DOCUMENTS

| | | | |
|---|---|---|---|
| 1,119,437 | 12/1914 | Lautz | 81/283 |
| 2,319,024 | 5/1943 | Wehringer | 285/84 |
| 2,341,003 | 2/1944 | Watson | 285/86 |
| 3,484,121 | 12/1969 | Quinton | 285/242 |
| 3,859,837 | 1/1975 | Burroughs | 72/410 |
| 3,924,635 | 12/1975 | Hakim | 604/9 |
| 4,610,683 | 9/1986 | Vaillancourt | 604/405 |
| 4,635,972 | 1/1987 | Lyall | 285/242 |
| 4,690,435 | 9/1987 | Manning et al. | 285/256 |
| 4,696,879 | 9/1987 | Lichte | 604/283 |
| 4,726,612 | 2/1988 | Picton | 285/256 |
| 4,774,940 | 10/1988 | Linder | 604/284 |
| 4,790,832 | 12/1988 | Lopez | 604/283 |
| 4,804,212 | 2/1989 | Vyse | 285/256 |
| 4,816,016 | 3/1989 | Schulte et al. | 604/9 |
| 4,876,788 | 10/1989 | Steer et al. | 29/508 |
| 4,880,414 | 11/1989 | Whipple | 604/283 |
| 5,042,974 | 8/1991 | Agarwal | 604/9 |

(List continued on next page.)

FOREIGN PATENT DOCUMENTS

| | | | |
|---|---|---|---|
| 722855 | 3/1932 | France | 81/9.3 |
| 718973 | 3/1942 | Germany | 81/9.3 |

OTHER PUBLICATIONS

Connectors for Neurosurgical Use, Heyer Schulte pamphlet 100681–002–04–779.
CSF–Flow Control Shunts, Pudenz–Schulte Medical pamphlet 10158–2, Feb. 1990, pp. 27–47.
Ebrahim, N.A., Coombs, R.E., Jackson, T. & Zeiss, Jr. The Effect of Metallic Implants on Magnetic Resonance Imaging, The Journal of Bone and Joint Surgery, 73–A, No. 9 pp.1397–1398, (Oct. 1991).

(List continued on next page.)

*Primary Examiner*—Corrine McDermott
*Attorney, Agent, or Firm*—J. Michael Martinez de Andino; McGuire, Woods, Battle & Boothe LLP; Jeffrey C. Lew

[57] ABSTRACT

An apparatus for draining cerebrospinal fluid from the ventricle of a brain includes an inner rigid tube and an outer flexible, elastic tube. The proximal end of the flexible tube has perforations to admit fluid into the elastic tube lumen in which the fluid is conducted to the distal end where the fluid exits into the remainder of a drain system, such as a ventriculoperitoneal shunt. The rigid tube contains an elbow bend intermediate the ends. In one form of the apparatus, the rigid tube has a first tubing nipple near one end and a second nipple intermediate the first nipple and the elbow bend. The first nipple extends outside and beyond the distal end of the flexible tube. The second nipple can be used to fasten the flexible tube to the rigid tube. The fastening method can employ a circumferential ligature as with suture thread or with a novel non-elastically deformable sleeve type of compression fitting. When implanted, the intercranial portion of the drain cannula descends directly into the ventricle from a burr hole in the skull and the extracranial portion remains flush adjacent the skull under the scalp. The rigid tube maintains the lumen in a patent condition at the burr hole despite the substantial angle between the distal and proximal portions of the flexible tube. The location of the two nipples permits fastening of the rigid tube to the flexible tube and joinder of the drain cannula to the drain system to be accomplished completely outside the burr hole.

11 Claims, 8 Drawing Sheets

U.S. PATENT DOCUMENTS

| | | | |
|---|---|---|---|
| 5,171,046 | 12/1992 | Iwata et al. | 285/331 |
| 5,176,627 | 1/1993 | Watson | 604/8 |
| 5,199,751 | 4/1993 | Beagle et al. | 283/256 |
| 5,304,114 | 4/1994 | Costman et al. | 604/8 |
| 5,312,337 | 5/1994 | Flaherty et al. | 604/93 |
| 5,385,541 | 1/1995 | Kirsh et al. | 604/8 |
| 5,387,188 | 2/1995 | Watson | 604/8 |
| 5,405,339 | 4/1995 | Kohnen et al. | 604/283 |
| 5,520,632 | 5/1996 | Leveen et al. | 604/9 |
| 5,632,734 | 5/1997 | Galel et al. | 604/282 |
| 5,725,493 | 3/1998 | Avery et al. | 604/9 |

OTHER PUBLICATIONS

Ebrahim, N.A., Salvolaine, E.R., Zeiss, J., & Jackson, T., Titanium Hip Implants for Improved Magnetic Resonance and Computed Tomography Examinations, Clinical Orthopaedics and Related Research, No. 275, pp. 194–198, (Feb. 1992).

Rupp, R. Ebrahim, N.A., Salvolaine, E.R., & Jackson, T., Magnetic Resonance Imaging Evaluation of the Spine With Metal Implants: General Safety and Superior Imaging with Titanium, Spine, 18 No. 3, pp. 379–385(1993).

Salvolaine, E.R., Ebrahim, N.A., Andreshak, T.G. & Jackson, T., Anterior and Posterior Cervical Spine Fixation Using Titanium Implants to Facilitate Magnetic Resonance Imaging Evaluation, Journal of Orthopaedic, Trauma, 3, No. 4, pp. 295–299 (1989).

Shellock, F.G., MR Imaging of Metallic Implants of Materials: A Compilation of the Literature, AJR 151, pp. 811–814, (1988).

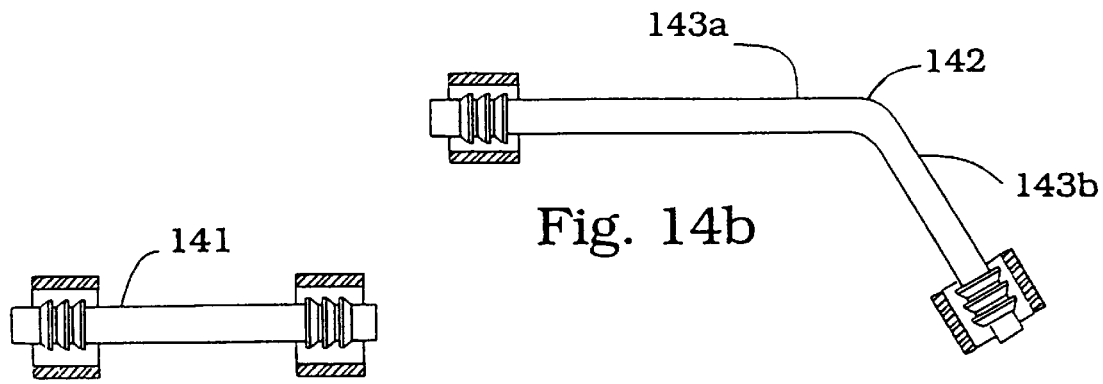
Fig. 14b
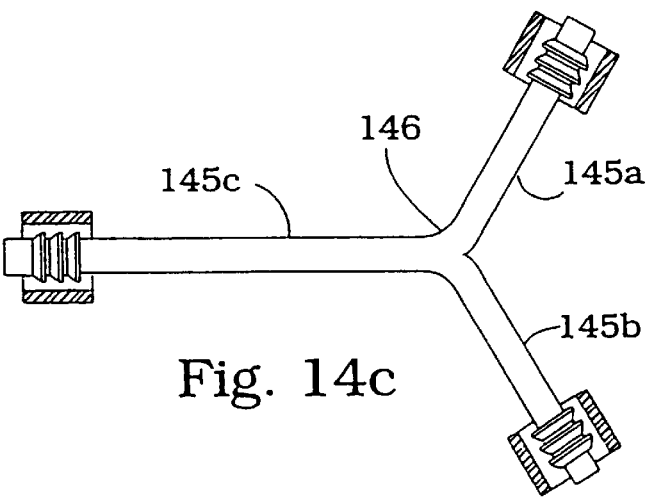
Fig. 14a
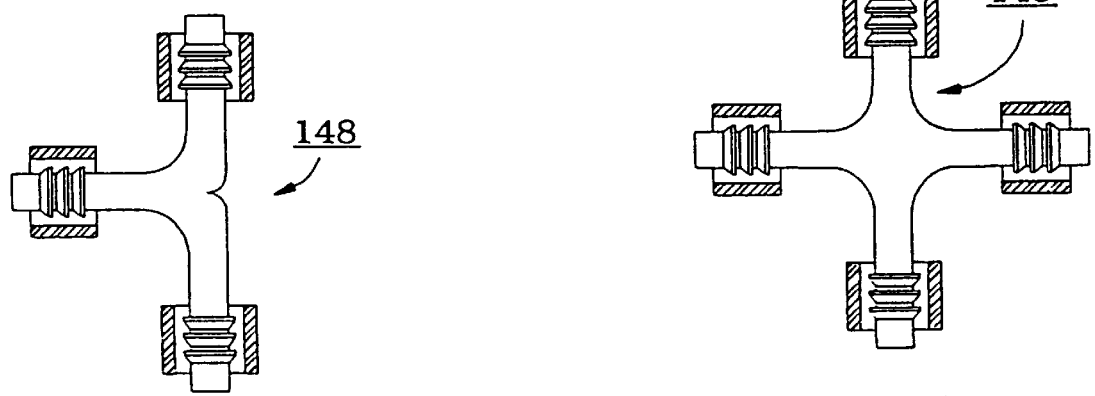
Fig. 14c
Fig. 14d
Fig. 14e

DRAIN CANNULA

This application is a continuation-in-part of U.S. application Ser. No. 08/505,807, filed Jul. 21, 1995 now U.S. Pat. No. 5,772,261.

FIELD OF THE INVENTION

This invention relates to an improved method and connector for joining medical tubes which conduct fluid from one location in the body to another or between a location in the body and an external location. Preferably, it relates to tube connections for ventriculoperitoneal shunts.

BACKGROUND AND SUMMARY OF THE INVENTION

When appropriately indicated, modern medical treatment frequently includes the procedure of moving fluid from one location in the body to another or between the body and an external apparatus. In a ventriculoperitoneal (VP) shunt for treating hydrocephalus, among other conditions, cerebrospinal fluid (CSF) is transferred from a ventricle of the brain to a receiving reservoir, such as the heart or peritoneum. A basic VP shunt system typically includes a proximal cannula for draining fluid from the ventricle, a subcutaneously implanted pressure valve connected to the proximal cannula, and a distal cannula connected subcutaneously between the pressure valve and the reservoir. The shunt may include other instruments, such as a flushing device and an injection port for administration of medicine or extraction of fluid samples.

Generally shunts employ thin walled, small diameter rubber tubes to conduct fluid throughout the shunt system. A common technique for joining two tubes together or for joining a cannula to an instrument uses a connector fitting with a tubular, cylindrical nipple. The nipple has a larger outer diameter than the inner diameter of the tube being joined. Inserting the nipple into the lumen of the tube stretches the tube walls, and produces a radially compressive force which forms a liquid tight seal between the tube and the nipple due to the elasticity of the tube.

It is extremely important that the tube does not disconnect from the nipple unexpectedly. For a subcutaneously implanted tube, accidental tube disconnection is particularly undesirable because surgical procedures are needed to make repairs. Although tube wall stretching provides some resistance against the tube disconnecting from the nipple, surgeons customarily tie one or more circumferential ligatures of suture thread around the tube at each nipple to increase resistance. However, if the ligature is too tight, the thread can cut through the tube wall, and in time, partially or completely sever the tube. In tying the ligature too tightly, the physician can also move the instrument out of position which sometimes causes the shunt to malfunction. If the ligature is too loose, it will not help to keep the tube on the nipple. Because ligatures are tied manually, whether or not the ligature tension is proper depends a great deal on the skill and dexterity of each treating physician.

VP shunt connection ligatures are more difficult to tie properly when the incision is small and the connection is partially hidden under the skin. This commonly happens when a previously implanted shunt is repaired. In order to remove an old knot and tie a new one, the physician usually enlarges the incision to provide adequate access. Large incisions take longer to heal, cause more discomfort and generally disfigure more than small incisions. Therefore, physicians must sometimes make incisions larger than desirable in order to manually ligate a tube connection.

Subcutaneous tube connections secured by ligatures also present the disadvantage that scar tissue tends to grow around the ligature. Scar tissue growth can anchor the tube-to-nipple joint to the body, which restricts free movement of the instrument within the patient. As the patient grows, the instrument can be pulled out of position or the tube can break or pinch. Excessive scar growth around the ligature also often makes it difficult to surgically revise a shunt.

In another aspect, the present invention relates to the medical tube connector material of construction. Conventional subcutaneous VP shunt connectors are made of stainless steel or nonmetallic materials, such as polymers. Although adequate for fluid transfer purposes, nonmetallic materials are not radioopaque. Consequently, it is difficult to verify position of the connectors subsequent to implantation. Stainless steel connectors are radioopaque, but they can distort magnetic resonance images (MRI). MRI scanning is an increasingly popular tool for noninvasive, internal soft tissue evaluation.

Another aspect of the present invention relates primarily to a proximal cannula of a VP shunt. The proximal cannula is usually a tube with a right angle elbow bend between the ends to form two arms. One arm of the tube is inserted into a ventricle of the brain through a hole drilled in the skull for this purpose. The second arm is placed outside and adjacent the skull for connection to a subcutaneously implanted shunt pressure valve. A conventional proximal cannula is made by bending a normally straight, flexible tube. Due to the rubbery nature of the tube, the inserted arm tends to return to a straight orientation causing the arm to withdraw from the ventricle or pinch against the rim of the hole. If the physician overbends the tube, i.e., to an acute angle, the tube can kink and occlude. Sometimes a right angle clip such as is available from Pudenz-Shulte Medical, Goleta, Calif., is mounted on the tube to impress a right angle bend in the tube. However, the clip is bulky and thus can produce an unsightly bump under the patient's skin after implantation. A proximal cannula can also be fashioned from two straight sections of tube joined to the ends of a rigid, right angle, elbow connector. Such cannulae suffer from the drawback that the ligated joint between the end of the tube inserted in the ventricle and the elbow is intradural. When such a shunt system is revised, the intradural tube tends to disconnect from the elbow. Also, revision typically requires dissection of scar tissue growth around the intradural ligature. This often causes undesirable bleeding in the region of the skull hole. According to the present invention, an angled shunt connector has been discovered which includes an extradural nipple for the intradural tube of a proximal cannula.

Therefore, it is an object of the present invention to provide a method for joining medical tubes which is more resistant to unexpected disconnection than connections secured by ligatures.

It is another object of the present invention to provide a medical tube connector for securing a medical tube with uniform consistency. The medical tube connector according to the present invention features an apparatus which can be used to clamp the tube onto a nipple to a preselected tightness. The invention thus provides the advantage that connections made by different physicians can be secured to an effectively identical extent. It is another advantage that the individual manual dexterity of the physician has less influence on the effectiveness of the connection.

It is still another object of the invention to provide a medical tube connector which allows the physician to connect a tube to a nipple when the joint is partially hidden under the skin. Use of the novel medical connector features the ability to secure a tube while reducing the extent of the incision.

It is a further object of the present invention to provide a titanium or titanium alloy medical tube connector for subcutaneous implantation which is radioopaque and which does not interfere with MRI techniques.

It is a still further object of this invention to provide a drain cannula for a VP shunt which provides a low profile, patent, right angle elbow connector which obviates the need for a intradural ligation.

Accordingly, there is now provided an apparatus for draining cerebrospinal fluid from a ventricle of a brain comprising:

(a) a tube connector including
   (1) a rigid, tubular body having a body outer diameter, the tubular body defining a central, longitudinal bore;
   (2) an elbow bend in the tubular body defining an intradural arm extending from the elbow bend to one body end and an extradural arm extending from the elbow bend away from the intradural arm defining at least one other body end;
   (3) a first nipple near the at least one other body end, at least a portion of the first nipple having a nipple outer diameter larger the body outer diameter;
   (4) a second nipple between the elbow bend and the first nipple, at least a portion of the second nipple having a nipple outer diameter larger than the body outer diameter; and (b) an elastically deformable flexible tube having a distal end, a proximal end opposite the distal end, a lumen emerging from the distal end, and ports at the proximal end for admitting fluid into the lumen; the flexible tube being concentrically mounted on the tube connector to form a fluid tight, lap joint of the distal end of the flexible tube and the second nipple with the elbow bend and intradural arm within the lumen and the first nipple protruding from the lumen at the distal end of the flexible tube, thereby orienting the proximal end at an angle relative to the extradural arm and establishing a fluid passageway through the lumen at the elbow bend.

BRIEF DESCRIPTION OF THE DRAWINGS

FIG. 13a is an end view of the connector of FIG. 13 taken along line 13a—13a.

FIG. 14a is a side view of a novel straight double ended tube connector wherein nipples at opposite ends are spaced apart.

FIG. 14b is a side view of a novel angled tube connector.

FIG. 14c is a side view of a novel Y-shaped medical tube connector.

FIG. 14d is a side view of a novel T-shaped medical tube connector.

FIG. 14e is a side view of a novel cross-shaped medical tube connector.

DETAILED DESCRIPTION

Figure 18:
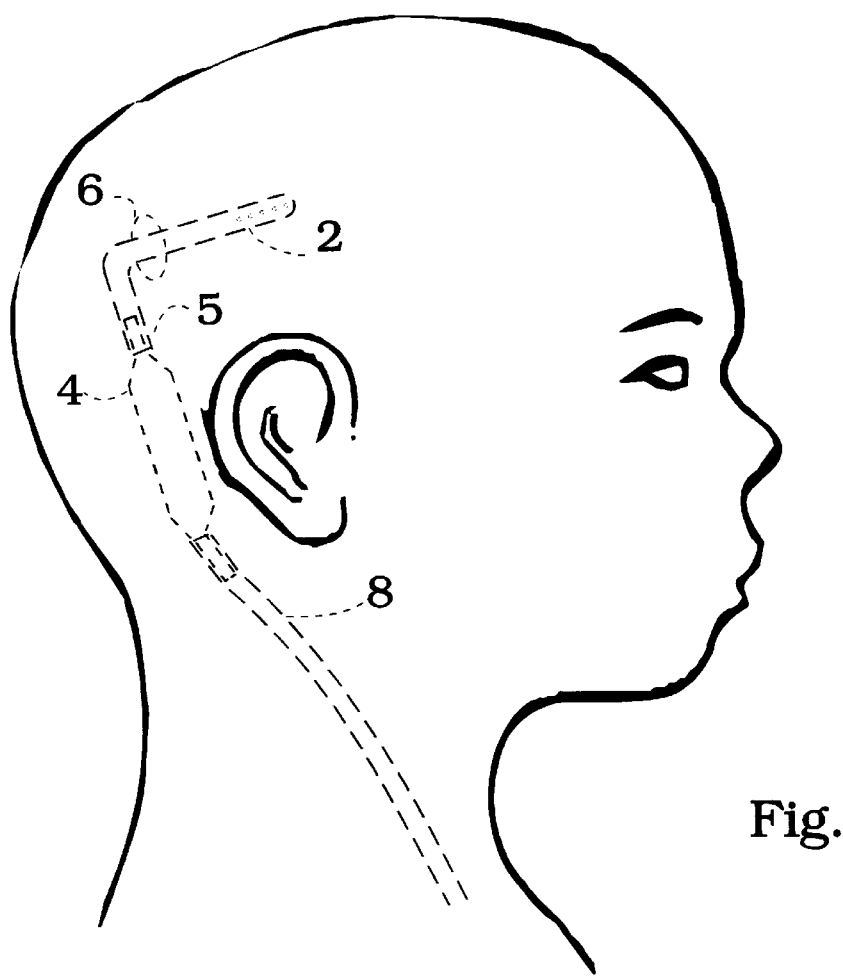
FIG. 18 is a diagram of a typical ventriculoperitoneal shunt.

The medical tube connector of the present invention is useful in a ventriculoperitoneal (VP) shunt, such as the type illustrated in FIG. 18. The shunt normally includes a proximal cannula 2 which extends through a hole 6 drilled in the skull into a ventricle of the brain, not shown. The shunt also usually includes a pressure valve 4 for controlling the pressure of cerebrospinal fluid (CSF), and a distal cannula 8 for transferring CSF to another location within the body or to an external fluid reservoir. Often, the shunt includes various subcutaneously implanted fluid transfer instruments such as pressure valves, anti-siphoning flow control valves, flushing devices and injection ports, (hereinafter collectively referred to as "shunt instruments" or "fluid transfer instruments") interconnected by segments of flexible, generally rubber tube. Generally, the terms "proximal" and "distal" as used herein with respect to elements of the claimed invention respectively mean portions of an apparatus near to and far from the source of fluid in the patient, that is, the ventricle of the brain with regard to a VP shunt.

Figure 1:
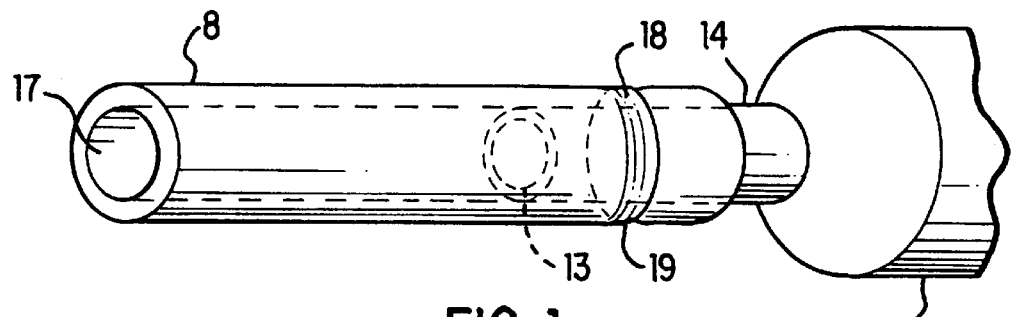
FIG. 1 is a perspective view of a conventional, ligature tied shunt tube connection.

A conventional connection of a VP shunt tube 8 to the body 12 of a fluid transfer instrument is shown in FIG. 1. The instrument has a generally tubular connection member 14 with a bore 13 in fluid communication with the interior of the body for conducting fluid to or from the instrument. The connection member is inserted into the lumen 17 of the tube to make the connection. A suture thread 18 is looped around the overlapped member, manually tightened and ligated with a knot, not shown, to form a tube constriction 19. If the ligation is too tight, motion of the patient over time can cause the thread to cut through the tube wall and fluid to leak out.

Figure 2:
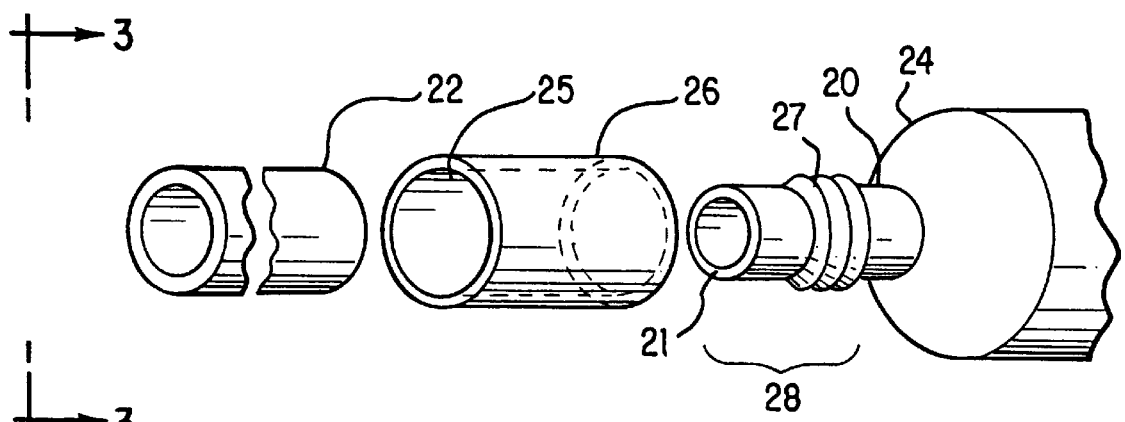
FIG. 2 is an exploded, perspective view of an embodiment of the medical tube connector according to the present invention.
Figure 3:
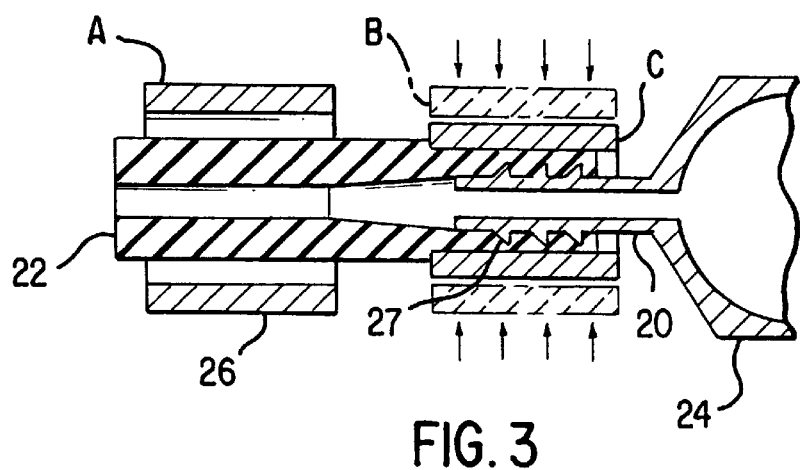
FIG. 3 is a section view taken along line 3—3 of FIG. 2.

A medical tube coupling according to the present invention can be understood with reference to FIGS. 2 and 3. The coupling includes a rigid, tubular member 20 having an internal bore 21 in fluid communication with the body 24 of a fluid transfer instrument. The end of the tubular member distant from the instrument forms a nipple 28. The nipple is generally a circular cross section tube of constant outer diameter, however, other shapes are contemplated. For example, the nipple can be frustoconical or it can have one or more circumferential, outwardly radiating sealing ridges 27. The ridges can be rounded and all the sealing ridges can have the same dimensions or they can vary in size with distance from the end of the connection member. For example, the sealing ridge proximal to the end can have the smallest outer diameter and the ridge most distant from the end can have the largest outer diameter. A plurality of frustoconical cross section sealing ridges is preferred. The nipple is adapted to insert snugly into lumen of shunt tube 22.

Accordingly, at least a portion of the nipple has an outer diameter larger than the diameter of the lumen when the tube is in a relaxed state. The tube typically is of a flexible, elastically deformable material. Inserting the nipple into the lumen causes the tube to stretch around the nipple. The elastic deformation creates a lap joint between the tube and the nipple. The lap joint provides a liquid tight seal and some radial tension which increases resistance of the tube to disconnect from the nipple.

The novel medical tube coupling additionally includes a generally cylindrically tubular sleeve 26 of a nonelastically deformable material. Non-elastically deformable means that the sleeve material is capable of being deformed to a new shape upon application of sufficient mechanical force, and the sleeve substantially maintains the new shape after the mechanical force is removed. Prior to deformation according to the method of this invention, the sleeve has an internal cavity 25 which is sufficiently large to receive the lap joint. That is, the sleeve fits loosely around the lap joint and is spaced apart by a radial distance from the outside surface of the tube. Upon application of a suitable, radially inwardly directed force to deform the sleeve tightly against the lap joint, the sleeve will clamp the tube to the nipple, thereby enhancing resistance of the tube to disconnect.

Operation of the novel medical tube coupling according to the method of the present invention can be understood with reference to FIG. 3. Prior to making the connection, tube 22 and tubular member 20 are axially displaced apart. At this time a free end of tube 22 can be threaded through the cavity of sleeve 26 and moved to a convenient location A distant from the end of the tube to be joined to the nipple. Next the end of the nipple can be inserted into the lumen of the flexible tube. The nipple is inserted to a sufficient distance to form a lap joint between the nipple and the tube by stretching the tube over portion of the nipple that is larger in diameter than the lumen diameter. In FIG. 3 the nipple includes an optional series of three, circumferential, outwardly radiating, frustoconical cross section sealing ridges 27.

When the tube stretches over the nipple, the sealing ridges act as teeth which project into the tube wall to effectively engage and further increase resistance of the tube to disconnect. Next, the sleeve is placed around the lap joint by sliding the sleeve to position B, shown in phantom. The sleeve can slide over the lap joint because the cavity is large enough to provide an annular gap between the sleeve and tube. The gap is greatly exaggerated in FIG. 3 for the sake of clarity. In practice the gap should be just large enough to let the sleeve move axially along the tube.

The sleeve is next compressed under externally applied force represented schematically by the arrows. The compressive force is sufficient to deform the sleeve until the tube is clamped between the nipple and the sleeve, but short of damaging the tube. The clamping force of the sleeve compresses the tube wall and provides enhanced resistance to disconnection from the nipple. Optionally, the surface of the sleeve facing the tube can be textured or can include radially inward directed projections to bite into the tube when the sleeve is deformed. This bite further increases the resistance of the tube to disconnect from the nipple.

According to the present invention the amount of deformation of the sleeve is important to achieve an effectively secure joint. While the flexible tube can be cut by overtightening the sleeve, the present invention provides the great advantage over a manually tied ligature that the extent of deformation can be controlled to prevent damage of the tube. For example, control can be achieved by compressing the sleeve in incremental steps using any conventional vise-like crimping tool, such as ordinary pliers. The extent of deformation can be checked after each step to assure that the sleeve is not too tight. The sleeve will maintain deformation after withdrawing compression force between steps because the sleeve material is nonelastically deformable. The treating physician can continue to compress the sleeve stepwise until the tube is deemed to be joined securely without damaging the tube.

One method of gauging the adequacy of sleeve deformation at each step is by visual inspection of the coupling. According to the present invention, the sleeve can also be deformed to the proper amount using a tool adapted for this purpose. The advantages of using the tool are that the sleeve can be compressed in a single, quick step, and that the treating physician can precisely and consistently apply a preselected amount of deformation. Also, in a preferred embodiment, the tool allows the treating physician to reach a medical tube coupling in confined spaces without the need to expand the incision much beyond the size required for admitting the tool. The tool should be selected to apply the correct amount of deformation required by specific nipple, tube and sleeve dimension combinations. That is, the combination of inner and outer diameters of the sleeve, tube and nipple will determine how much sleeve deformation is needed to effectively clamp the tube without damaging it. The treating physician will know the dimensions of the components in advance and thus can select a tool appropriately designed to precisely impart the predetermined amount of deformation.

Figure 4:
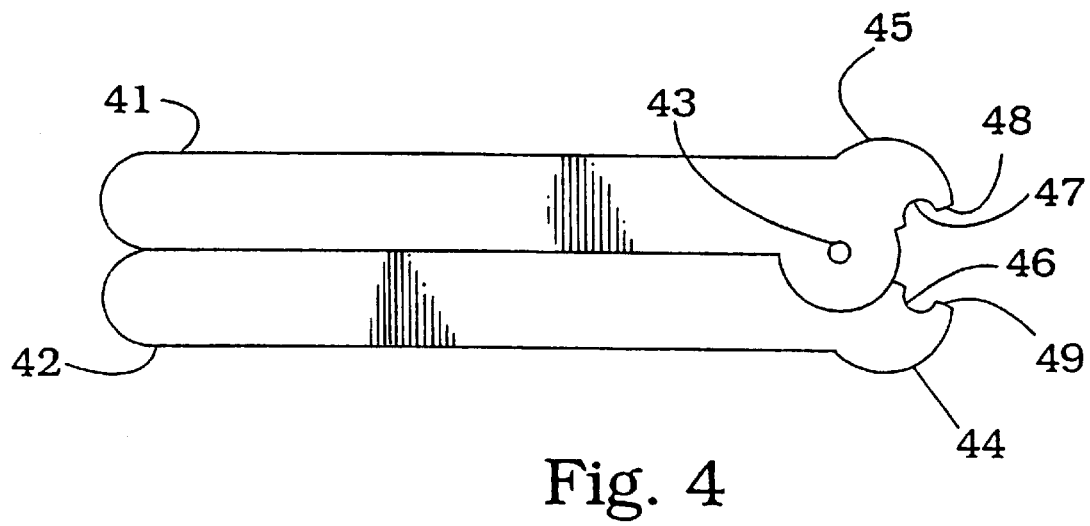
FIG. 4 is a side view of one embodiment of a clamping tool in a jaw open position.
Figure 5:
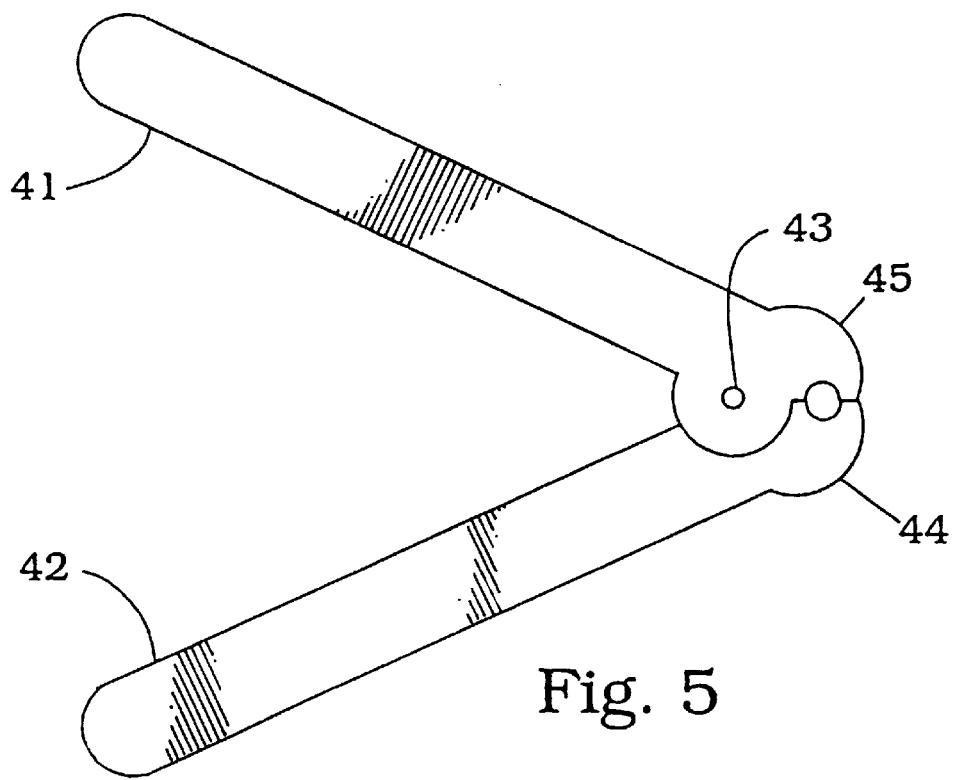
FIG. 5 is a side view of the clamping tool of FIG. 4 in a jaw closed position.

A crimping tool according to the present invention is shown in FIGS. 4 and 5. The tool has a pair of handles 41 and 42 for gripping the tool. The handles also operate in hinged lever fashion about pivot pin 43 to actuate opposing jaws 44 and 45. Each jaw has a generally semicylindrical concave compression surface 46 and 47. In an open position, FIG. 4, the jaws are separated by a distance large enough to admit the uncompressed medical tube coupling. The jaws can be closed toward each other by manipulation of the handles, FIG. 5. As the jaws close, the compression surfaces engage the sleeve, causing it to deform. The jaws can continue to close until movement is limited by interference between stopping faces 48 and 49, also shown in FIG. 7. The stopping faces are positioned to prevent excessive deformation that would damage the tube. For any combination of sleeve, tube and connection member sizes, it should be a simple matter for one of ordinary skill in the art without undue experimentation to determine how much the jaws should close to clamp the tube without damaging it. After the tube is clamped, the jaws are opened to release the coupling.

Figure 6:
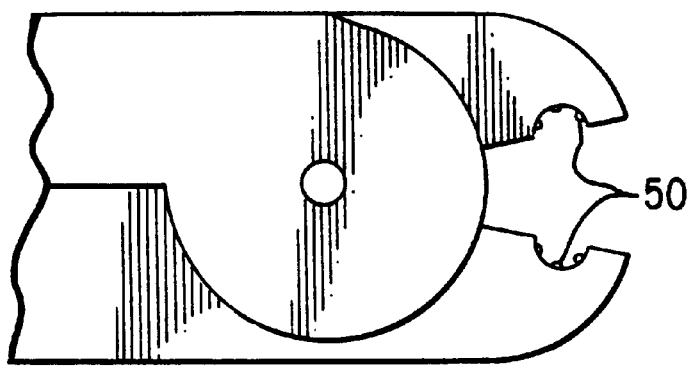
FIG. 6 is a partial side view of another embodiment of a clamping tool according to the present invention.
Figure 8:
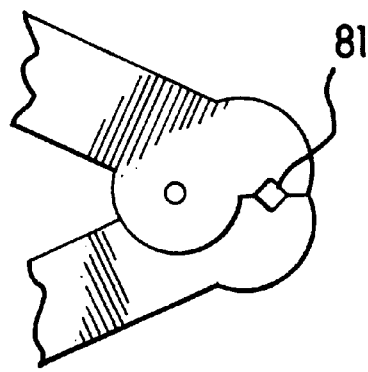
FIG. 8 is a partial side view of a clamping tool wherein the jaw faces are flat to define a polygonal cavity.
Figure 7:
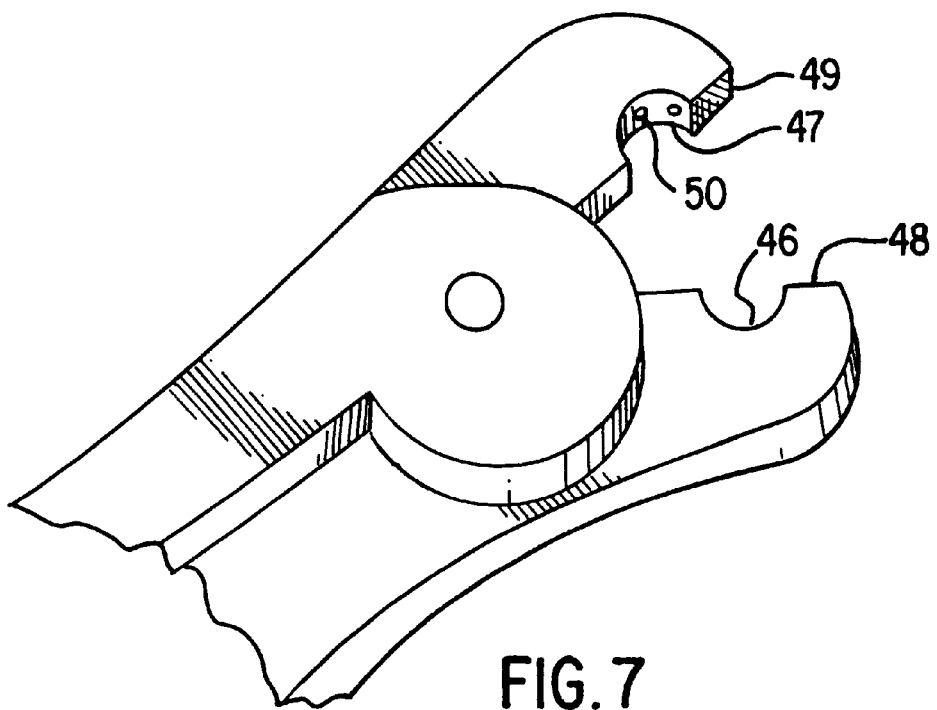
FIG. 7 is a partial perspective view of the clamping tool shown in FIG. 6.

A preferred embodiment of the crimping tool is illustrated in FIGS. 6 and 7. A plurality of protrusions 50 are disposed circumferentially around the concave compression surfaces 46 and 47. The purpose of the protrusions is to concentrate the deformation at selected sites located uniformly around the tube so that deflection is precisely controlled to the depth necessary to clamp the tube. The protrusions can be any shape, such as spherical and frustoconical. The protrusions can be ridges, i.e., curvilinear corrugations in contrast to discrete points. The peaks of the protrusions should be sufficiently blunt to avoid piercing the sleeve and tube. In a particularly preferred embodiment, three spherical protrusions are disposed circumferentially 60 degrees apart on each of two opposite jaws, FIG. 6. The jaw faces can also have facets to define a polygon-shaped compression surface 81, as shown in FIG. 8.

Figure 9:
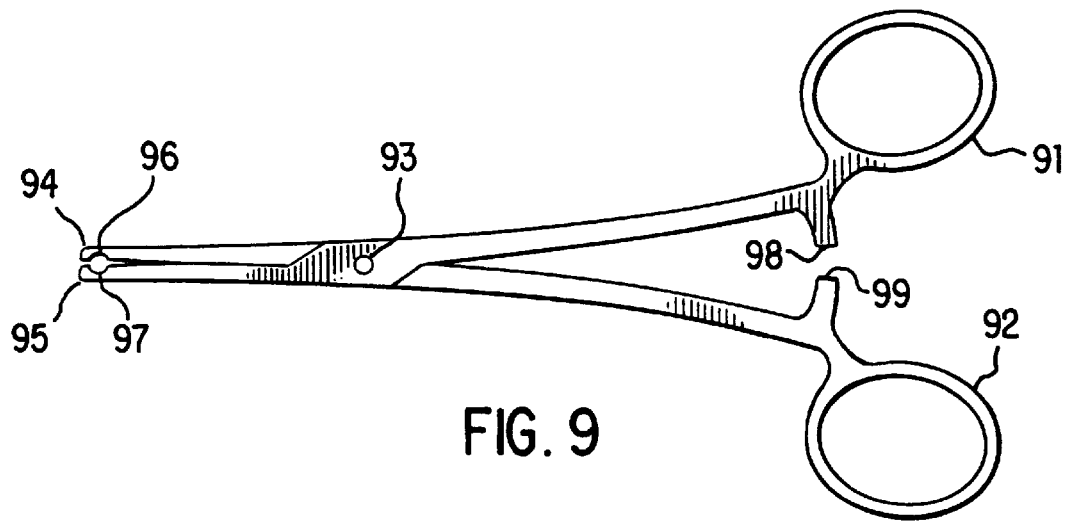
FIG. 9 is a side view of clamping tool with a needle nose jaw configuration.

A preferred, hemostat design crimping tool illustrated in FIG. 9 can enable the physician to clamp couplings in locations that are normally inaccessible for manually tied ligations, such as within small incisions and under skin flaps. Needle nose shaped jaws, 94 and 95, contain concave compression surfaces 96 and 97. In this embodiment, the handles 91 and 92 pivot on pin 93 in scissors action to open the jaws by separating the handles and to close the jaws by bringing the handles together. Stop faces 98 and 99 limit the approach of the jaws to control the maximum deformation of the compressed sleeve.

Figure 10:
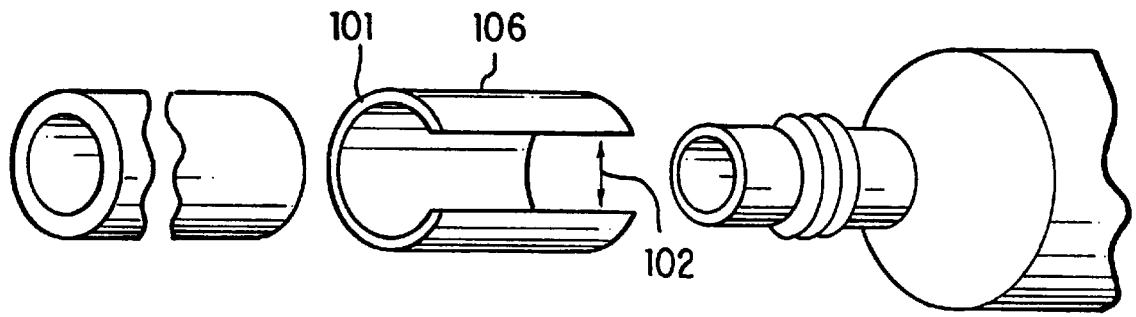
FIG. 10 is a perspective view of a medical tube connector with a C-shaped sleeve.

Variations of the basic medical tube connector disclosed above are contemplated within the scope of the present invention. In a preferred embodiment, shown in FIG. 10, the sleeve 106 is an incomplete cylinder, such as can be manufactured by cutting a section of rigid tube longitudinally from end to end, or by rolling a metal strip on a mandrel. The sleeve thus will have a C-shaped cross section 101 with a gap 102 between the top and bottom of the "C". By selecting a C-shaped sleeve with a suitably wide gap, the sleeve can be placed around a previously connected tube and nipple joint without disconnecting the tube. This feature is particularly advantageous for revising previously implanted couplings. A previously clamped sleeve can be removed by expanding or cutting it, and a new sleeve can be installed while the tube remains on the nipple.

Figure 11:
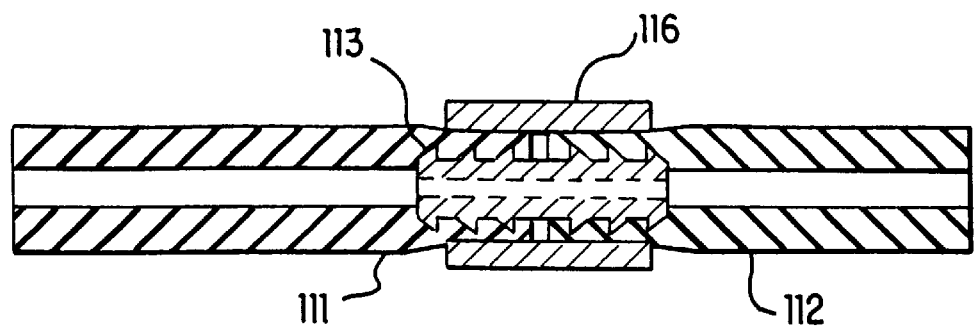
FIG. 11 is a section view of a straight, double ended tube connector according to this invention.

In one aspect, the present invention provides a novel medical tube connector. Tube connectors are useful typically for splicing together multiple tubes. A connector with only two ends on a tubular body can be used to combine two shorter tubes to produce a single, longer tube. The body of such a connector is generally cylindrical and has an internal bore extending between the ends. FIG. 11 illustrates in section view a preferred double ended, straight, rigid medical tube connector 113 joining two segments of flexible tube 111 and 112 according to the present invention. The connector includes a single, nonelastically deformable sleeve 116 to clamp both tube segments to the connector. Because the two connector nipples are close, a single sleeve is sufficient to clamp both tubes. Optionally the nipples can be spaced apart axially by a length of rigid tube. Then an individual sleeve at each nipple can be deployed to provide a coupling.

Figure 12:
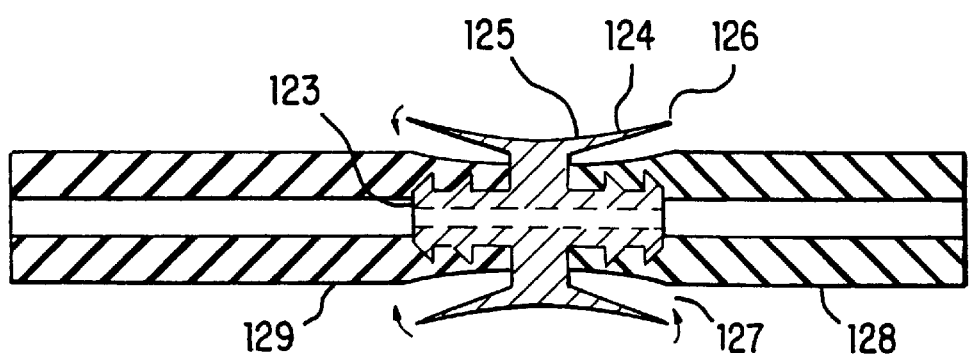
FIG. 12 is a section view of a straight, double ended tube connector wherein the sleeve is integral to the tube connection member.

In another preferred embodiment the sleeve and nipple are unitary as shown in FIG. 12. The sleeve comprises a plurality of elongated tabs 124 disposed circumferentially about the coupling and each tab is fixed at one end 125 to the connector body. Opposite ends 126 of the tabs are initially spaced apart from the nipple to form cavities 127. An end of each tube, 128 and 129, is slid over a nipple of the connector and is extended into the cavity. The tube is then clamped by depressing the spaced apart ends of the tabs radially inward to engage the tube as shown by the arrows in FIG. 12.

Figure 13:
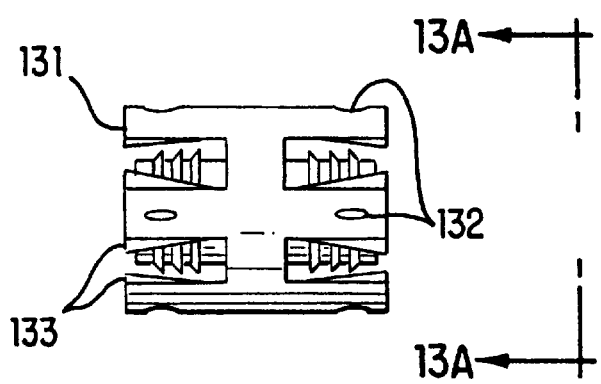
FIG. 13 is a side view of a straight, double ended tube connector wherein the sleeve is integral to the tube connection member and wherein tabs include dimples.
Figure 13A:
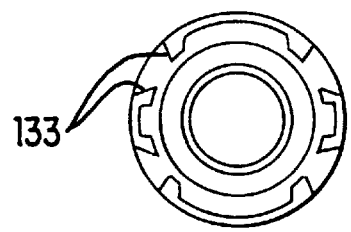

A side elevation of another unitary, double ended connector is shown in FIGS. 13 and 13a. Each of the tabs 131 includes at least one dimple 132 adapted to receive protrusions of a crimping tool. A crimping tool as described above can be used to depress the tabs in a precise and controlled manner to a sufficient deformation to effect clamping without damaging the tube. In a medical tube connector having tabs according to the present invention, preferably about 3–6, equally spaced tabs are disposed on the circumference of the coupling. The figures illustrate that the tabs include optional extensions 133. Each extension protrudes radially inward and circumferentially outward from its parent tab. The size of the extensions is selected so as to ultimately interfere with the neighboring extension on an adjacent tab when the tabs are deformed. Interference between neighboring extensions thus limits the clamping deformation of the tabs thereby preventing the tabs from excessively constricting and thereby damaging the tube.

FIGS. 14a–14e illustrate various medical tube connector configurations according to the present invention. FIG. 14a shows a straight, double ended connector with a length of tube 141 separating the nipples and a novel coupling at each nipple. FIG. 14b shows an angled, double ended connector having a single elbow bend 142 located on the tubular body between the ends. Straight segments between a bend and each end, or between adjacent bends in multiple bend connectors are referred to as arms. Thus, the angled connector has arms 143a and 143b. Connectors having more than two ends are illustrated in FIGS. 14c–e. Segments of such connectors meet at a junction and segments between junctions and each end are referred to as legs. Accordingly, the Y-shaped connector of FIG. 14c contains three legs, 145a, 145b and 145c meeting at junction 146. Similarly, T-shaped connector 148 and cross shaped connector 149 have three and four legs, respectively. Multiple legged connectors can also include one or more elbow bends. According to this invention the novel medical tube coupling is used on these tube connectors.

Figure 15:
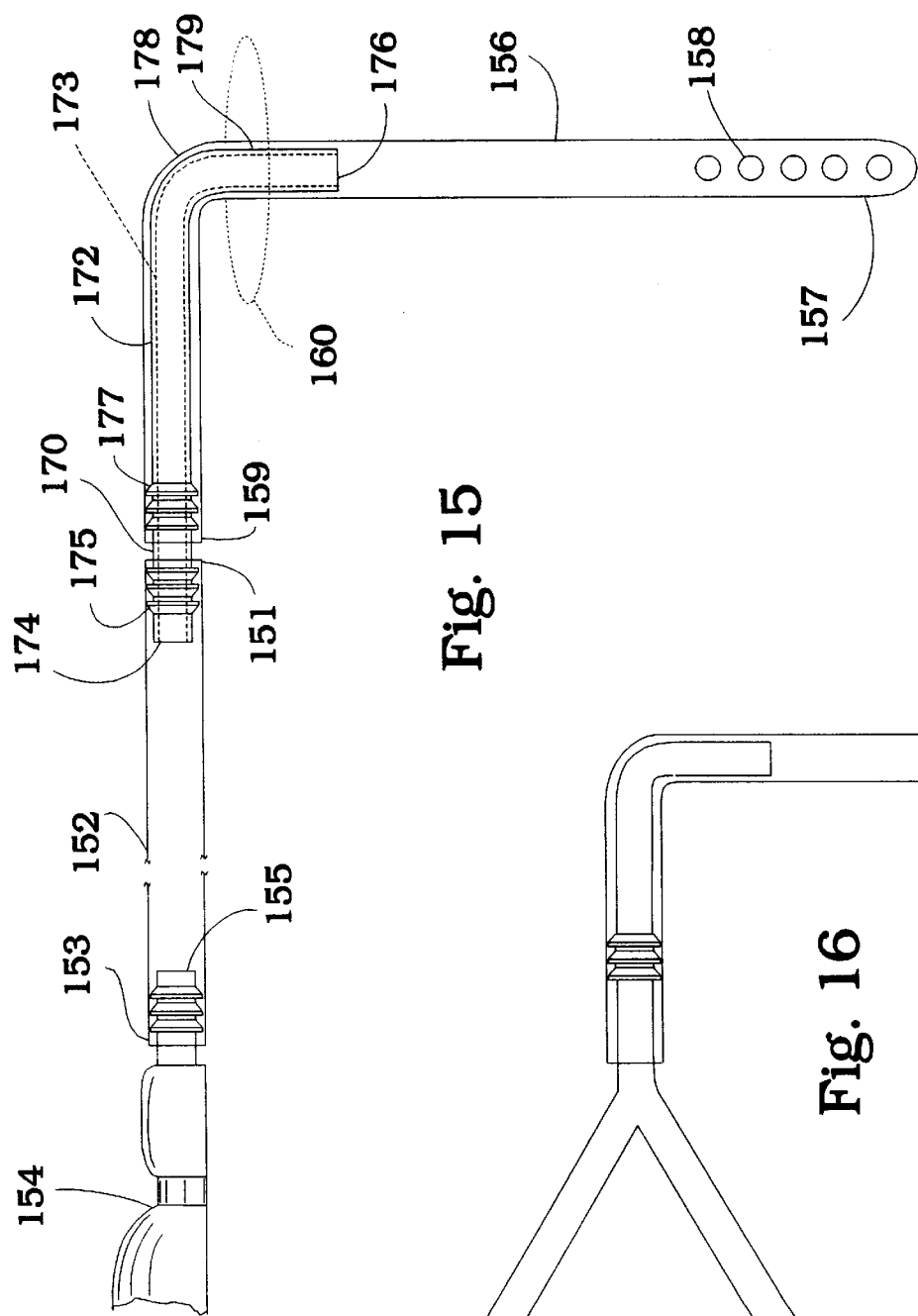
FIG. 15 is a view of a proximal cannula of a VP shunt using a novel, angled medical tube connector.

In another aspect the present invention includes a novel, angled medical tube connector preferably for use in a proximal cannula of a VP shunt, FIG. 15. The proximal cannula comprises a first flexible, elastically deformable tube 152 the lumen of which communicates at a distal end 153 with a port 155 of a fluid flow instrument such as a pressure valve 154. The pressure valve and tube are generally implanted just under the scalp and should have low profiles to provide the patient with as natural appearance as possible. The first tube 152 thus lies adjacent the skull as it leads toward the skull hole 160. The proximal cannula further comprises a second flexible tube 156 which extends at its proximal end 157 into a ventricle of the brain, not shown. The proximal end 157 of the second flexible tube includes means, such as perforations 158 in the tube wall for drawing cerebrospinal fluid from the ventricle into the bore of the tube. Normally, the second flexible tube 156 is disposed substantially perpendicularly to the first flexible tube 152 and the tubes meet in a sharp bend near the skull hole. In order to maintain the lumen patent as it turns the bend, the proximal cannula further includes the novel angled, tube connector 170 which splices together the proximal end 151 of the first flexible tube 152 and the distal end 159 of the second flexible tube 156. The angled tube connector 170 has a rigid, generally tubular body with an internal bore 173 extending between first connector end 174 and second connector end 176. The angled tube connector 170 includes a substantially right angle elbow bend 178 at a distance from both the first and second connector ends.

First flexible tube 152 joins to connector 170 at a first nipple 175 suitably sized to cause the tube to stretch over the nipple as the connector end is inserted into the lumen of the tube. The nipple can have optional sealing ridges as previously described. The angled tube connector of this invention further includes a second nipple 177 for joining to the second flexible tube. This connector distinguishes over conventional connectors primarily by including the second nipple 177 at a location on the tubular body in the arm between the first nipple 175 and the elbow bend 178. To connect the second flexible tube to the second nipple, the second connector end 176 is inserted into the lumen at the distal end 159. Then the second tube is pushed over the connector arm 179, around the elbow bend 178, over the other connector arm 172 and over the second nipple 177. Therefore, it is seen that the lap joint between the second flexible tube and the second nipple is outside and substantially distant from the skull hole. This advantageously provides that the tube can be secured to the connector extradurally and obviates the difficulties caused by intradural connections mentioned above.

Figure 16:
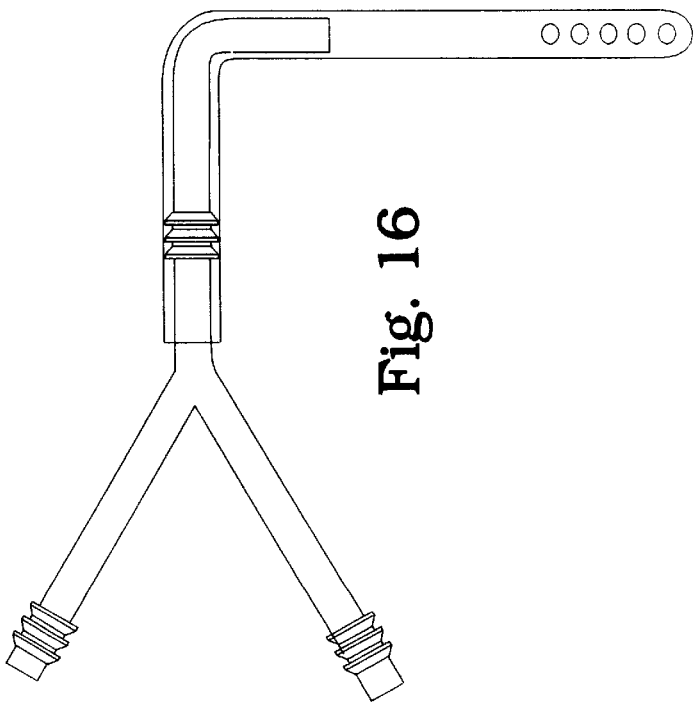
FIG. 16 is a perspective view of a novel Y-shaped, angled medical tube connector.

The nipples can each include one or more sealing ridges of various shapes adapted to resist disconnection of the tubes from the angled connector. For example, cross sections of the ridges can be semicircular or frustoconical. If it is desired to connect multiple shunt instruments to the novel angled connector, the extradural portion of the connector can include multiple legs. For example, a Y-shaped connector is illustrated in FIG. 16. Similarly, T-shaped, cross-shaped, and other manifold connector configurations are contemplated.

Figure 17:
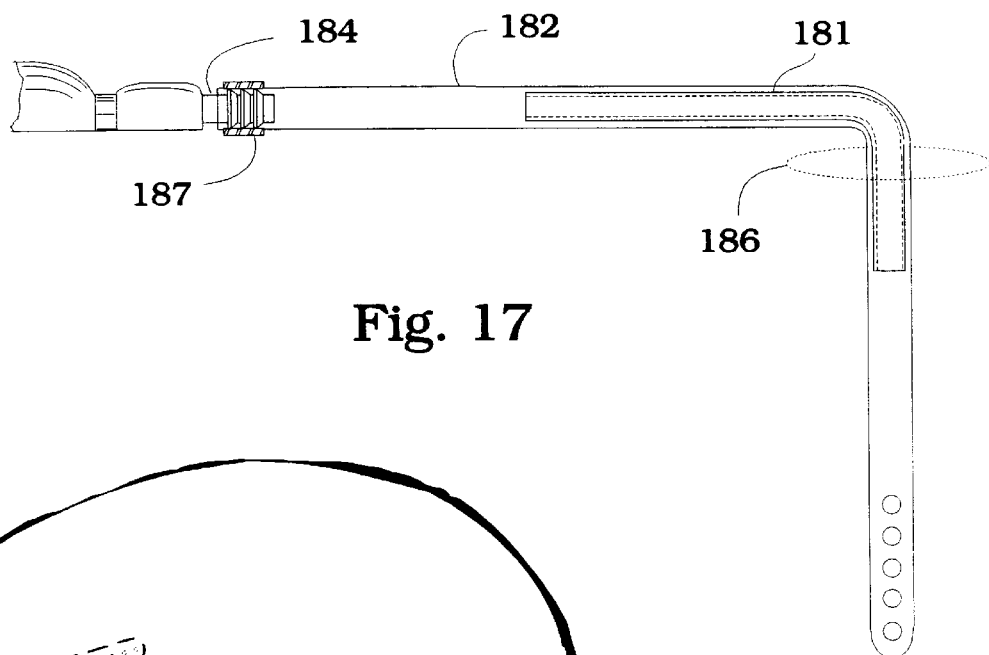
FIG. 17 is a view of a novel medical tube connector having a smooth outer surface for a proximal cannula of a ventriculoperitoneal shunt.

In another aspect the novel angled medical tube connector for a proximal cannula of the present invention includes a smooth outer surface, substantially right angled elbow connector, shown in FIG. 17. The flexible tube 182 is slipped completely over the connector 181 which resides entirely within the lumen of tube. The flexible tube end is joined directly to the shunt instrument 184. Preferably, a medical tube connector according to this invention is used to secure the flexible tube to the instrument. This embodiment provides the advantage that separate joints between flexible tubes and the angled connector are eliminated. The connector remains in position because the intradural arm is inserted in the skull hole 186. The tube does not disconnect from the connector because it extends over the connector and into the ventricle.

In still another aspect of the present invention, the embodiments illustrated in FIGS. 15–17 can be advantageously used as a drain cannula for draining cerebrospinal fluid from the ventricle of the brain of a patient. The elbow bend of the rigid tubular body being positioned within the flexible tube orients the distal portion of the tube at an angle relative to the proximal portion of the flexible tube while maintaining an open fluid passageway between the perforations and the distal end of the tube. Thus, the distal portion of the tube can be implanted outside and adjacent to the skull while the proximal portion descends at substantially a ninety degree angle relative to the distal portion into the ventricle. While it is quite desirable to clamp the flexible tube with a nonelastically deformable sleeve to the nipple of the rigid tubular body and to other implanted fluid transfer instruments of a VP shunt system, the benefits of the novel drain cannula also can be obtained without using the sleeve. For example, the tube can be secured to the nipple with a conventional, manually tied ligature of suture thread. That is, a suture as in FIG. 1 can be substituted for the sleeve 187 in FIG. 17.

The nondeformable portion of the novel medical tube connector can be made of any effectively rigid, biologically compatible material. Plastic, such as polyester, polyolefin, and polyamide engineering plastics, and non-corroding metals, such as stainless steel are suitable. It is preferred that the connector be of material that is radiographically detectable but which does not interfere with magnetic resonance imaging (MRI). Connectors of titanium or titanium alloy are preferred. The nonelastically deformable, sleeve material should be capable of changing shape when moderate force is applied, and of retaining the deformed shape when the force is removed. Non-corroding, ductile metals, such as stainless steel, are suitable. Titanium is a preferred sleeve material because it is radioopaque but does not interfere with MRI, as mentioned. Connectors of strong metallic materials provide the additional advantage that wall thicknesses can be thinner than needed for connectors of weaker materials. Connectors with thin walls provide increased lumen size, and consequently, improved fluid flow, without substantially changing outer diameter. For example, it is expected that a conventional, nonmetallic connector of 1.0 mm inner diameter and 1.9 mm outer diameter can be replaced with a 2.0 mm inner diameter 2.5 mm outer diameter titanium connector to provide improved flow.

The novel medical tube connector is also useful in medical connector applications other than those in which a tube connection is subcutaneously implanted. For example, a connector according to this invention can be used for securing tube connections in dialysis treatment, or blood or urine transfer procedures.

What is claimed is:

1. A method of using a drain cannula to drain cerebrospinal fluid from a ventricle of a brain comprising:
    (I) implanting in a patient the drain cannula including
        (a) a tube connector comprising
            (1) a rigid, tubular body having a body outer diameter, the tubular body defining a central, longitudinal bore;
            (2) an elbow bend in the tubular body defining an intradural arm extending from the elbow bend to one body end and an extradural arm extending from the elbow bend away from the intradural arm defining at least one other body end;
            (3) a first nipple near the at least one other body end, at least a portion of the first nipple having a nipple outer diameter larger the body outer diameter;
            (4) a second nipple between the elbow bend and the first nipple, at least a portion of the second nipple having a nipple outer diameter larger than the body outer diameter; and
        (b) an elastically deformable flexible tube having a distal end, a proximal end opposite the distal end, a lumen emerging from the distal end, and ports at the proximal end for admitting cerebrospinal fluid into the lumen; the flexible tube being concentrically mounted on the tube connector to form a fluid tight, lap joint of the distal end of the flexible tube and the second nipple with the elbow bend and intradural arm within the lumen and the first nipple protruding from the lumen at the distal end of the flexible tube
    (II) orienting the proximal end into the ventricle at an angle relative to the extradural arm;
    (III) orienting the distal end outside and adjacent to the skull of the patient; and
    (IV) tying a thread circumferentially around the lap joint to secure the flexible tube to the second nipple.

2. The method of claim 1 wherein the angle is about 90 degrees.

3. An apparatus for draining cerebrospinal fluid from a ventricle of a brain comprising:
   (a) a bent tube including
      (1) a non-deformable, rigid, tubular body having a uniform body outer diameter, the tubular body defining a central, longitudinal bore;
      (2) an elbow bend in the tubular body defining an intradural arm extending from the elbow bend to one other body end and an extradural arm extending from the elbow bend to one other body end wherein the elbow bend is formed as a curve having a fixed, predetermined radius; and
   (b) an elastically deformable flexible tube having a distal end, a proximal end opposite the distal end, a lumen emerging from the distal end, and ports at the proximal end for admitting fluid into the lumen; the bent tube being wholly within the lumen with the distal end of the flexible tube extending beyond the other body end of the bent tube, thereby orienting the proximal end at an angle relative to the extradural arm and establishing a fluid passageway through the lumen at the elbow bend.

4. The apparatus of claim 3 wherein the angle is about 90 degrees.

5. An apparatus for draining cerebrospinal fluid from a ventricle of a brain comprising:
   (a) a tube connector including
      (1) a rigid, tubular body having a body outer diameter, the tubular body defining a central, longitudinal bore;
      (2) an elbow bend in the tubular body defining an intradural arm extending from the elbow bend to one body end and an extradural arm extending from the elbow bend away from the intradural arm defining at least one other body end;
      (3) a first nipple near the at least one other body end, at least a portion of the first nipple having a nipple outer diameter larger the body outer diameter;
      (4) a second nipple between the elbow bend and the first nipple, at least a portion of the second nipple having a nipple outer diameter larger than the body outer diameter; and
   (b) an elastically deformable flexible tube having a distal end, a proximal end opposite the distal end, a lumen emerging from the distal end, and ports at the proximal end for admitting fluid into the lumen; the flexible tube being concentrically mounted on the tube connector to form a fluid tight, lap joint of the distal end of the flexible tube and the second nipple with the elbow bend and intradural arm within the lumen and the first nipple protruding from the lumen at the distal end of the flexible tube, thereby orienting the proximal end at an angle relative to the extradural arm and establishing a fluid passageway through the lumen at the elbow bend.

6. The invention of claim 5 wherein each nipple comprises at least one, outwardly radiating, circumferential sealing ridge defining a frustoconical shape forming teeth adapted to resist disconnection of a tube from the nipple.

7. The apparatus of claim 6 wherein the teeth of the first nipple are adapted to resist disconnection of a tube from a direction opposite to that of the second nipple.

8. The invention of claim 7 wherein the teeth of the first nipple are adapted to resist disconnection of a tube from the at least one other body end and the teeth of the second nipple are adapted to resist disconnection of the flexible tube from the extradural arm.

9. The apparatus of claim 5 wherein the extradural arm further comprises a plurality of branches, each branch having a branched end portion with said first nipple being disposed at said branched end portion, each said branch extending between a junction and said branched end with said junction being disposed intermediate said first nipple and said second nipple.

10. The apparatus of claim 9 wherein each first nipple comprises at least one, outwardly radiating, circumferential sealing ridge defining a frustoconical shape forming teeth adapted to resist disconnection of a tube from the nipple toward the branched end, and wherein the second nipple comprises at least one, outwardly radiating, circumferential sealing ridge defining a frustoconical shape forming teeth adapted to resist disconnection of the flexible tube from the nipple toward the intradural arm.

11. The apparatus of claim 5 wherein the angle is about 90 degrees.

* * * * *

UNITED STATES PATENT AND TRADEMARK OFFICE
CERTIFICATE OF CORRECTION

PATENT NO. : 5,913,852

DATED : June 22, 1999

INVENTOR(S) : Gary Magram

It is certified that error appears in the above-identified patent and that said Letters Patent are hereby corrected as shown below:

Column 12, Line 12, Claim 6, after "The" delete "invention" and insert therefor --apparatus--
Column 12, Line 19, Claim 8, after "The" delete "invention" and insert therefor --apparauts--

Signed and Sealed this

Fourteenth Day of December, 1999

Attest:

Q. TODD DICKINSON

*Attesting Officer*     *Acting Commissioner of Patents and Trademarks*

UNITED STATES PATENT AND TRADEMARK OFFICE
CERTIFICATE OF CORRECTION

PATENT NO : 5,913,852
DATED : June 22, 1999
INVENTOR(S): Gary Magram

It is certified that error appears in the above-identified patent and that said Letters Patent is hereby corrected as shown below:

Column 12, line 12, Claim 6, after "The" delete "invention" and insert therefor --apparatus--.
Column 12, line 19, Claim 8, after "The" delete "invention" and insert therefor --apparatus--.

This certificate supersedes Certificate of Correction issued December 14, 1999.

Signed and Sealed this

Eleventh Day of April, 2000

Q. TODD DICKINSON

Attest:

Attesting Officer

Director of Patents and Trademarks